(12) United States Patent
Hunke et al.

(10) Patent No.: US 8,696,867 B2
(45) Date of Patent: Apr. 15, 2014

(54) DISULFO-TYPE FLUORESCENT WHITENING AGENTS

(75) Inventors: Bernhard Hunke, Hennef (DE); Andrei Tauber, Cologne (DE); Michael Kraemer, Kuerten (DE); Guenter Klug, Langenfeld (DE); Theo Lansing, Leverkusen (DE); Marco Hafermann, Bergisch Gladbach (DE)

(73) Assignee: Blankophor GmbH & Co. KG (DE)

( * ) Notice: Subject to any disclaimer, the term of this patent is extended or adjusted under 35 U.S.C. 154(b) by 0 days.

(21) Appl. No.: 13/496,678

(22) PCT Filed: Sep. 17, 2010

(86) PCT No.: PCT/EP2010/063699
§ 371 (c)(1),
(2), (4) Date: Apr. 23, 2012

(87) PCT Pub. No.: WO2011/033062
PCT Pub. Date: Mar. 24, 2011

(65) Prior Publication Data
US 2012/0211188 A1    Aug. 23, 2012

(30) Foreign Application Priority Data
Sep. 17, 2009   (EP) ...................................... 09170579

(51) Int. Cl.
*D21F 11/00*   (2006.01)
(52) U.S. Cl.
USPC .......................................................... 162/158
(58) Field of Classification Search
USPC ............................... 162/158; 8/648; 544/193.2
See application file for complete search history.

(56) References Cited

U.S. PATENT DOCUMENTS

| 6,143,889 | A  | * | 11/2000 | Metzger et al. | ............ | 544/193.2 |
| 6,210,449 | B1 | * | 4/2001  | Rohringer et al. | ................ | 8/648 |
| 6,723,846 | B1 | * | 4/2004  | Metzger et al. | ............ | 544/193.2 |
| 2002/0017001 | A1 | * | 2/2002  | Rohringer et al. | ................ | 8/648 |
| 2005/0120490 | A1 | * | 6/2005  | Metzger et al. | ............... | 8/115.51 |
| 2007/0107137 | A1 | * | 5/2007  | Metzger et al. | ............... | 8/115.51 |
| 2008/0073617 | A1 | * | 3/2008  | Cockcroft et al. | ....... | 252/301.23 |
| 2008/0191169 | A1 | * | 8/2008  | Rohringer et al. | ....... | 252/301.25 |

FOREIGN PATENT DOCUMENTS

| EP | 1752453 | 2/2007 |
| EP | 09170579.8 | 9/2009 |
| WO | 9842685 | 10/1998 |
| WO | 0119804 | 3/2001 |
| WO | 02055646 | 7/2002 |
| WO | 03078724 | 9/2003 |
| WO | 2011033062 | 9/2010 |

OTHER PUBLICATIONS

International Search Report issued in International Application No. PCT/EP2010/063699 dated May 12, 2011; 5 pages.
Notification Concerning Transmittal of the International Preliminary Report on Patentability issued in International Application No. PCT/EP2010/063699 dated Mar. 29, 2012; 8 pages.

* cited by examiner

*Primary Examiner* — Mark Halpern
(74) *Attorney, Agent, or Firm* — Cantor Colburn LLP

(57) ABSTRACT

Concentrated aqueous fluorescent whitening agent preparations are disclosed for optically whitening paper, wherein the preparation contains a specific disulfo-type fluorescent whitening agent.

9 Claims, 2 Drawing Sheets

DISULFO-TYPE FLUORESCENT WHITENING AGENTS

CROSS-REFERENCE TO RELATED APPLICATIONS

This is a U.S. National Stage of Application No. PCT/EP2010/063699 filed on Sep. 17, 2010. Priority under 35 U.S.C. §119(a) and 35 U.S.C. §365(b) is claimed from European Patent Application No. 09170579.8, filed on Sep. 17, 2009, the disclosure of which is also incorporated herein by reference.

This application is a 371 of PCT/EP10/63699 filed 17 Sep. 2010.

BACKGROUND

The present disclosure relates to the use of specific disulfo-type fluorescent whitening agents for whitening paper or board.

It is well known that the whiteness of paper and board can be improved by the addition of fluorescent whitening agents (FWAs). The most important FWAs used in the paper and board industry are anilino-substituted bistriazinyl derivatives of 4,4'-diaminostilbene-2,2'-disulfonic acid (flavonic acid). From these FWAs disulfo-, tetrasulfo- and hexasulfo-types are known. The disulfo-type FWAs with no sulfonic acid groups at the aniline rings have a low solubility in water and a high affinity for cellulose fibres. They are especially suitable for use at the wet-end of paper making process. The hexasulfo-type FWAs with two sulfonic acid groups at each aniline ring have a high solubility in water and a low affinity for cellulose fibres. They are more specialty products when very high whiteness is desired. The tetrasulfo-type FWAs with one sulfonic acid group at each aniline ring exhibit a behaviour between the disulfo- and hexasulfo-type FWAs and are most commonly used for whitening paper or board.

For ease of handling and metering, the paper and board industry demands FWAs to be supplied in a liquid form, preferably as a concentrated aqueous solution, which should be stable to prolonged storage over a wide temperature range. Due to the low solubility of disulfo-type FWAs in water, currently solubilising auxiliaries such as urea, triethanolamine or diethylene glycol are added in amounts of up to 30% to provide storage stability for concentrated aqueous solutions of disulfo-type FWAs. These solubilising agents have no affinity to cellulose and contaminate the effluent from the paper mill, thus being undesired. EP-A-1 752 453 teaches storage stable solutions of disulfo-type FWAs which contain specific counter-ions for the sulfonic acid groups, which counter-ions are derived from specific aminoalkanols. WO 02/055646 A1 discloses concentrated aqueous solutions containing a mixture of two specific disulfo-type FWAs.

Alternatively, slurries or dispersions of disulfo-type FWAs in water are known, e.g. from EP 0 884 312 B1. However, in order to enable the metering of homogenous preparations into the papermaking process, usually stirring is required.

BRIEF SUMMARY

Surprisingly, it has been found that problems of the prior art can be overcome by using concentrated aqueous preparations of specific disulfo-type fluorescent whitening agents having carboxylic acid groups at the aniline rings for whitening paper or board. These disulfo-type fluorescent whitening agents enable stable concentrated aqueous preparations or solutions to be formed, without addition of solubilising auxiliaries. Moreover, the production process of those fluorescent whitening agents is more cost-effective, compared to that of the commonly used disulfo-type fluorescent whitening agents, since it dispenses with laborious isolation and filtration steps.

Therefore, the present invention relates to the use of aqueous fluorescent whitening agent (FWA) preparations for optically whitening paper or board, wherein the fluorescent whitening agent preparation contains
(a) 5 to 80% by weight of at least one fluorescent whitening agent (FWA) selected from the bis(triazinylamino) stilbene derivatives of the general formula (I)

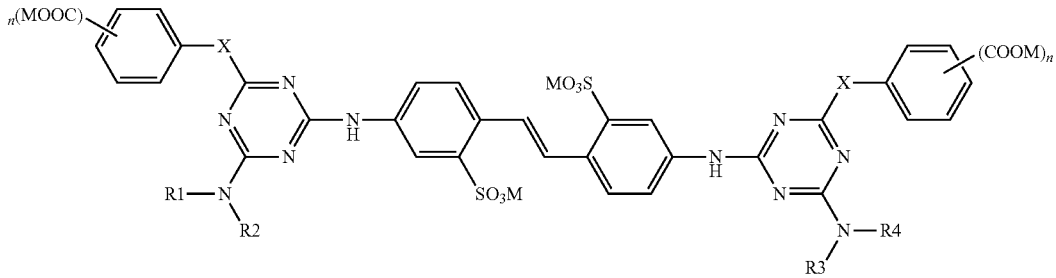

wherein X represents independently of each other O or NR', where R' is hydrogen or $C_1$-$C_3$ alkyl;
n is 1 or 2;
$R_1$, $R_2$, $R_3$ and $R_4$ represent, independently of each other, hydrogen, cyano, $C_1$-$C_4$ alkyl, $C_2$-$C_4$ hydroxyalkyl, or $C_1$-$C_4$ alkoxyalkyl, wherein alkyl is linear or branched; or $R_2$ and $R_1$ or $R_3$ and $R_4$ independently of each other together with N atom form morpholine, piperidine or pyrrolidine ring; or —$(CH_2)_l$—$SO_3M$, where l is 1, 2 or 3; or —$(CH_2)_i$—COOR, —$(CH_2)_i$—CONHR, —$(CH_2)_i$—COR, where i is an integer from 1 to 4, R is $C_1$-$C_3$ alkyl or has the same meaning as M;
M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl; and
(b) 95 to 20% by weight of water.

The invention also refers to the use of the aqueous fluorescent whitening agent (FWA) preparations for whitening paper in the pulp or at the surface. Further, the invention relates to a process for whitening paper and to paper obtainable by this process. Preferred embodiments of the invention are described in the description hereinafter, the figures and the claims.

BRIEF DESCRIPTION OF THE DRAWINGS

Referring now to the figures wherein the like elements are numbered alike.

DETAILED DESCRIPTION

Figure 1:
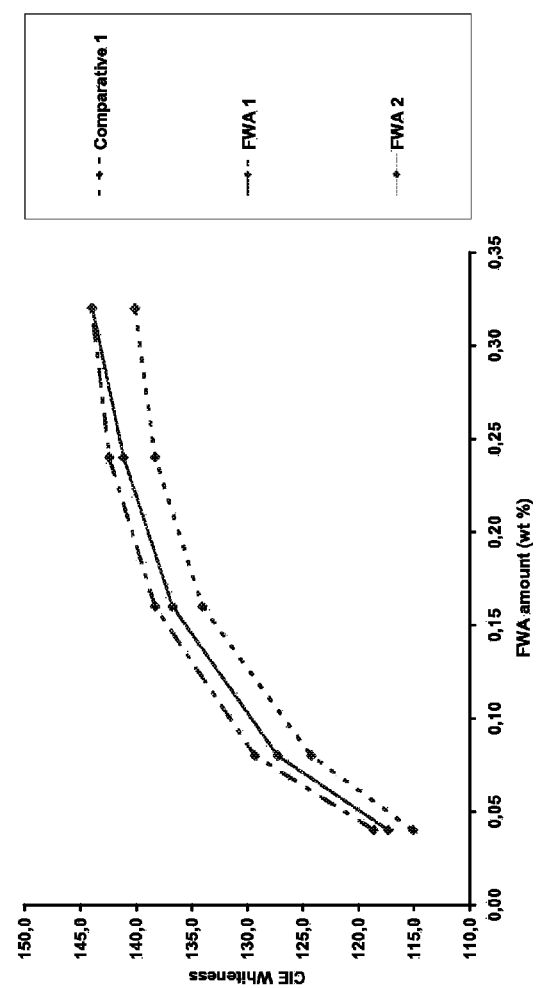
FIG. 1 is a diagram showing the whitening performance of different fluorescent whitening agents in wood-free pulp.

According to the disclosure, component (a) of the aqueous FWA preparation comprises at least one FWA of the above defined formula (I). In a preferred embodiment, X represents NR'. In another preferred embodiment, n is 1. In a further preferred embodiment, $R_1$, $R_2$, $R_3$ and $R_4$ represent, independently of each other, $C_2$-$C_4$ hydroxyalkyl, or $C_1$-$C_4$ alkoxyalkyl, wherein alkyl is linear or branched Embodiments of M are hydrogen, Na, K, Ca, Mg, in other embodiments, M is Na, K or hydrogen, and in still other embodiments, M is Na.

Exemplary FWAs are the FWAs of following formula (Ia) and formula (Ib), wherein the carboxylic acid residues are, independently of each other, in ortho- or para-position, preferably in para-position:

The purification of the FWAs of formula (I) is easier and thus more cost-effective than for commonly used disulfo-type FWAs, since isolation steps can be avoided. The purification could be carried out by, for example, membrane filtration. In contrast to the water evaporation or salt precipitation steps disclosed in PL patent 61710, the purification of the FWAs of formula (I) can be achieved by membrane filtration and the product obtained can be used as such. This is due to the surprisingly higher solubility of FWA of formula (I).

The aqueous FWA preparation used according to the disclosure can contain one or more FWAs of the formula (I). In one embodiment, the preparation contains one FWA of the formula (I). In another embodiment, the preparation contains two or three FWAs of the formula (I). It is also possible that other known FWAs are additionally used.

In one embodiment, the aqueous FWA preparation used according to the disclosure contains component (a) in an amount of 6 to 80% by weight, in other embodiments 7 to 80% by weight, in in yet other embodiments 8 to 75% by weight, in still other embodiments 9 to 70% by weight, and yet additional embodiments 10 to 65% by weight. The water (component (b)) can be contained in an amount of 94 to 20% by weight, in other embodiments 93 to 20% by weight, in still other embodiments 92 to 25% by weight, in still other

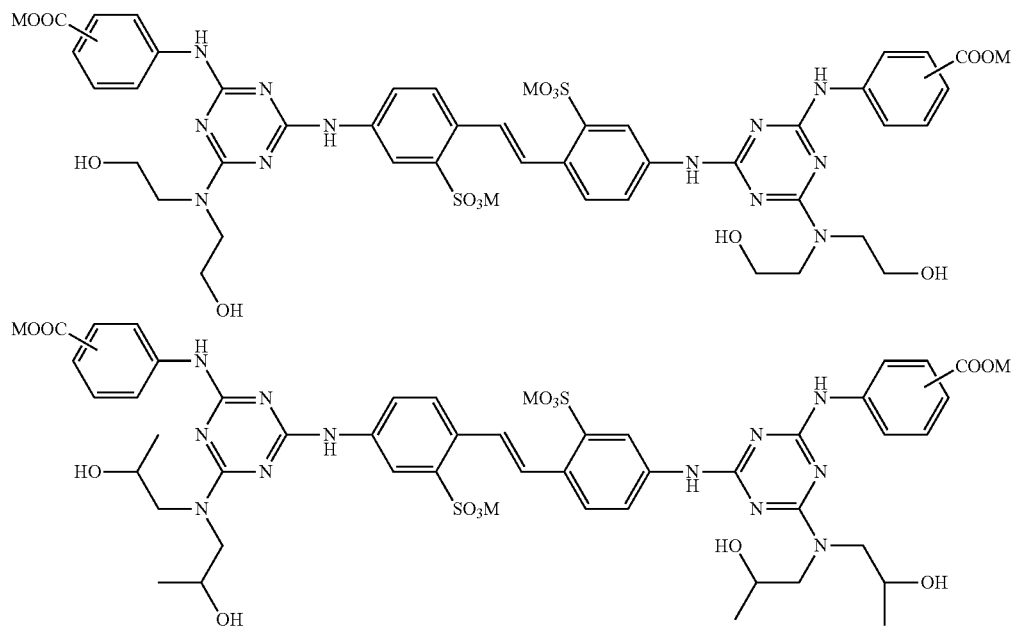

The FWAs of formula (I) can be prepared by known procedures, and are used as free acids or as salts thereof, preferably alkali metal salts. In the present disclosure, the compounds are prepared by reacting cyanuric chloride with 4,4'-diaminostilbene-2,2'-disulfonic acid or a salt thereof, and an appropriate carboxyl acid group containing derivative, e.g. amino benzoic acid. PL patent 61710 discloses the preparation of some specific FWAs of the above defined formula (I) with one carboxylic acid group in p-position of each aniline ring. GDR (DDR) patent 55 668 discloses a further process for preparing some specific FWAs of the above defined formula (I) with one or two carboxylic acid groups at each aniline ring.

embodiments 91 to 30% by weight, and yet other embodiments 90 to 35% by weight. In other embodiments, the aqueous FWA preparation contains 12 to 60% by weight, in other embodiments 15 to 55% by weight, in yet other embodiments 20 to 50% by weight, of component (a), and 88 to 40% by weight, in other embodiments 85 to 45% by weight, and in still other embodiments 80 to 50% by weight, of component (b). Unless otherwise indicated, the weight percentages herein are based on 100% by weight of the aqueous FWA preparation.

In one embodiment, the aqueous FWA preparations are free of crystalline whitener particles, in particular their hydrate forms.

The amount of component (a) in the aqueous FWA preparation may depend on the temperature of the preparation. Optionally, the aqueous FWA preparation used according to the disclosure may contain a small amount of auxiliaries. This might be particularly relevant for FWA preparations used in cold regions to enhance preparations' cold stability. In one embodiment, the aqueous FWA preparation contains less than 25% by weight, in other embodiments less than 20% by weight, in still other embodiments less than 15% by weight, and in yet other embodiments less than 10% by weight of components other than components (a) and (b). For example, formulation auxiliaries, such as standardizing agents, surface-active compositions, antifoams, organic thickeners, preservatives, and/or electrolytes may be used. However, for ecological reasons, the aqueous FWA preparation preferably contains only very small amounts of components other than components (a) and (b), e.g. organic additives or auxiliaries, particularly altogether less than 3% by weight, in particular less than 1% by weight, based on 100% by weight of aqueous FWA preparation. In one embodiment, the FWA preparation contains no organic co-solvents, and/or urea. In a further embodiment, the FWA preparation consists or consists essentially of components (a) and (b).

The aqueous FWA preparation is present in liquid form, in particular as a solution.

The aqueous FWA preparation can be prepared by introducing the at least one FWA of formula (I) in form of a powder or a concentrated solution thereof into water. Any auxiliaries can optionally be added during the preparation of the aqueous FWA preparation.

The aqueous FWA preparations can be used for whitening paper or board in the pulp suspension (stock) or pulp, in particular in the wet-end, or for applications to the surface. In wet-end applications the preparations can be added at any point of the pulp circuit, e.g. chests or pipes, before sheet forming. Depending on the papermaking process used, the preparations can be added to the papermaking process also in diluted form, wherein the preparation has been diluted to a desired concentration by addition of water and/or auxiliaries. In one embodiment, the aqueous FWA preparation is introduced, optionally after dilution with water, to the pulp or pulp suspension. The preparations can be added continuously or discontinuously. The application is beneficial for both wood-containing pulps and wood-free pulps.

The aqueous FWA preparations exhibit high storage stability and ease of application. Simultaneously, they provide high affinity (substantivity) to fibres and high whitening performance.

The disclosure also refers to a process for whitening paper, which comprises providing a pulp or pulp suspension; adding the aqueous FWA preparation to the pulp or pulp suspension, an amount of 0.01 to 5% by weight in some embodiments, and 0.02 to 2% by weight in other embodiments, based on dry pulp; producing a paper sheet from the pulp; and drying the sheet. The aqueous FWA preparation used in this process is the same aqueous FWA preparation as described above. In one embodiment of this process, the aqueous FWA preparation is added, after dilution with water and/or auxiliaries, in particular dilution with water, to the pulp or pulp suspension. Paper produced by using the aqueous FWA preparations exhibits higher whiteness and higher greening limit compared to typically used disulfo-type FWAs.

The whiteness of the papers produced can be characterized by the CIE whiteness. Different FWAs can be compared to each other with respect to the saturation behaviour when determined according to CIE whiteness. In other words, if a larger amount of FWA is used and no further increase in whiteness is found, there is saturation behaviour and there may even be adverse effects on the whiteness when using higher amounts. The effect of saturation is also referred to as greening. The greening limit, i.e. the point at which increasing amounts of FWA used results in virtually no further increase in whiteness, can be derived, for example, from the a*-b* diagram, where a* and b* are the colour coordinates in the CIE-L*a*b* system.

The following non-limiting examples illustrate the disclosure and show various embodiments without limiting the scope of protection.

EXAMPLES

Example 1

The solubility behaviour of two fluorescent whitening agents used according to the disclosure and of a comparative fluorescent whitening agent of the disulfo-type was studied. Further, the stability behavior of a concentrated aqueous solution was tested. 10% (w/w) solution of sodium hydroxide (222 g) was added dropwise to the reaction mixture to keep the pH at 4.5 while the mixture was heated up to 16° C.

The tested fluorescent whitening agents according to disclosure were the following:

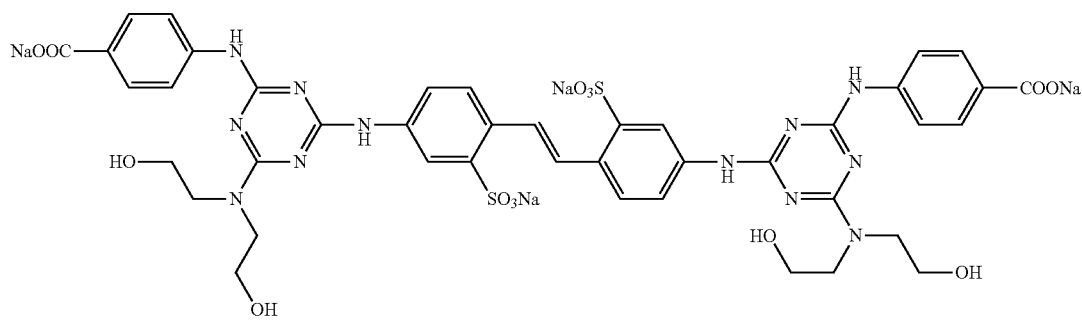

FWA 1

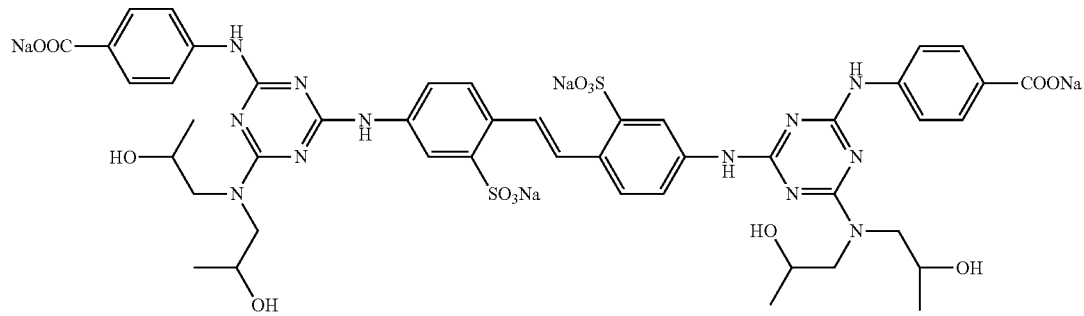

FWA 2

For comparison, the following, commonly used fluorescent whitening agent of the disulfo-type was used:

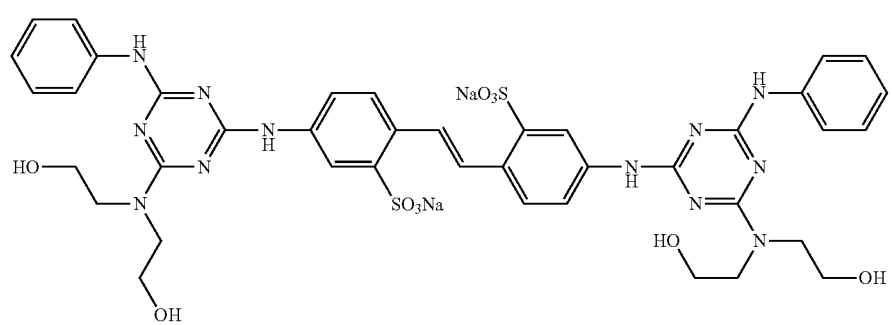

Comparative 1

The solubility of the fluorescent whitening agents was determined as follows: a dry powder of fluorescent whitening agent was added to 50 ml of distilled water until the saturation point was reached. The thus obtained saturated solution was filtered, dried and the dried residue was weighted.

The following results were obtained: 27.8% for FWA 1; 24.2% for FWA 2; and 6.9% for Comparative 1, all at ambient temperature (about 22° C.). The indicated percentages are based on the amount of grams of fluorescent whitening agent dissolved in 100 g of the corresponding saturated FWA solution.

The stability behavior was studied by storing an approximately 20% solution of FWA 1 and FWA 2, respectively, at ambient temperature and at 4° C., each without stirring. The aqueous brightener preparations have a shelf-life of more than 30 days both at ambient and low temperature. They showed no crystalline precipitates.

Thus, FWA 1 and FWA2 exhibit a much higher solubility than Comparative 1. Simultaneously, concentrated solutions thereof exhibit high stability.

Example 2

The whitening performance of the FWAs of Example 1 was studied using the following test procedure.

The wood-free furnish (pulp suspension) was composed of 70 pts (parts, based on weight) of short fibres and 30 pts of long fibres with a grinding degree of 30-35° SR (Schopper-Riegler). The wood-containing furnish was composed of 50 pts of mechanical pulp, 35 pts of long fibres and 15 pts of short fibres with a grinding degree of 40° SR. 800 ml of a 0.625% of corresponding furnish were weighted in a beaker to prepare a 5 g hand sheet of ~120 g/m² for each experimental series. A 0.1 wt % FWA solution was prepared using distilled water.

The amounts of FWA as indicated in Table 1 below were achieved by addition of a corresponding amount of the 0.1 wt % FWA solution by a pipette to the stirred pulp suspension which was allowed to stir for 10 minutes after FWA addition. The amounts of FWA in Table 1 are calculated as active ingredient on 100 wt % of dry pulp.

A wet filter paper was positioned on the wire of the sheet former, the stock is put on the sheet former and was sucked dry. The formed hand sheet was protected by an additional dry filter, pressed and dried on a calender at 100° C. Thereafter, the obtained hand sheets were equilibrated in a climate room under standard conditions overnight and then measured with a Datacolor spectrometer (ISO2469) by determining CIE, L*, a* and b*, the light source used based on ISO2469 standard.

Figure 2:
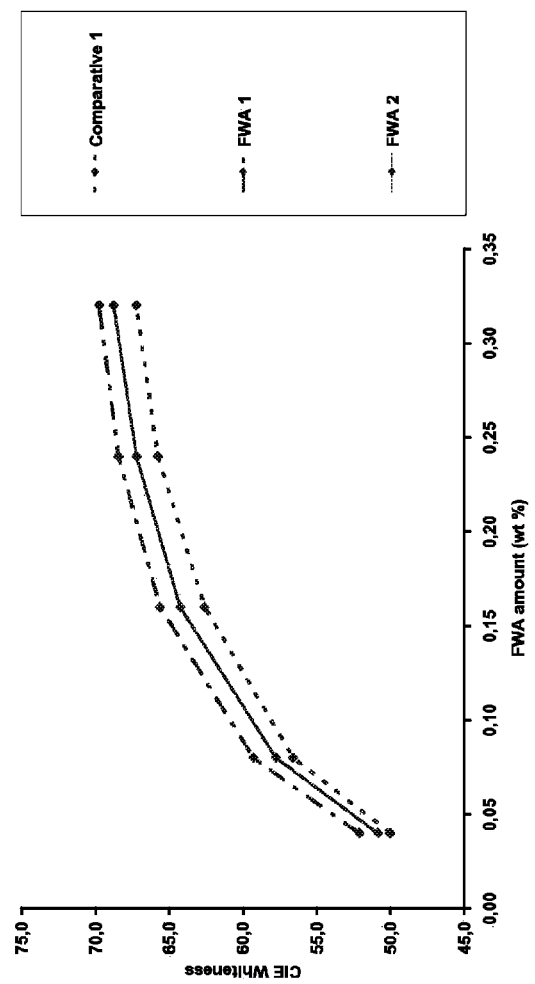
FIG. 2 is a diagram showing the whitening performance of different fluorescent whitening agents in wood-containing pulp.

The results obtained are summarized in Tables 1a and 1b and further shown in the Figures. FIG. 1 shows the results for the wood-free pulp and FIG. 2 for the wood-containing pulp.

TABLE 1a

| | Wood-free pulp | | | | |
|---|---|---|---|---|---|
| FWA | Amount (wt %) FWA | CIE whiteness | L* | a* | b* |
| FWA 1 | 0.04 | 118.59 | 97.15 | 1.89 | −5.83 |
| | 0.08 | 129.29 | 97.48 | 2.41 | −8.10 |
| | 0.16 | 138.27 | 97.76 | 2.69 | −10.03 |
| | 0.24 | 142.39 | 97.86 | 2.71 | −10.92 |
| | 0.32 | 143.96 | 97.93 | 2.57 | −11.25 |

TABLE 1a-continued

Wood-free pulp

| FWA | Amount (wt %) FWA | CIE whiteness | L* | a* | b* |
|---|---|---|---|---|---|
| FWA 2 | 0.04 | 117.27 | 97.22 | 1.86 | −5.49 |
| | 0.08 | 127.23 | 97.46 | 2.36 | −7.64 |
| | 0.16 | 136.69 | 97.68 | 2.74 | −9.70 |
| | 0.24 | 141.11 | 97.80 | 2.87 | −10.66 |
| | 0.32 | 143.91 | 97.74 | 2.86 | −11.33 |
| Comparative 1 | 0.04 | 115.09 | 97.13 | 1.71 | −5.04 |
| | 0.08 | 124.22 | 97.30 | 2.18 | −7.03 |
| | 0.16 | 134.02 | 97.61 | 2.54 | −9.12 |
| | 0.24 | 138.27 | 97.81 | 2.58 | −10.00 |
| | 0.32 | 140.10 | 97.89 | 2.51 | −10.38 |

TABLE 1b

Wood-containing pulp

| FWA 1 | 0.04 | 52.12 | 93.83 | −0.08 | 7.14 |
|---|---|---|---|---|---|
| | 0.08 | 59.30 | 94.08 | 0.22 | 5.72 |
| | 0.16 | 65.61 | 94.20 | 0.30 | 4.41 |
| | 0.24 | 68.43 | 94.31 | 0.22 | 3.85 |
| | 0.32 | 69.74 | 94.45 | 0.18 | 3.64 |
| FWA 2 | 0.04 | 50.86 | 93.84 | −0.10 | 7.42 |
| | 0.08 | 57.77 | 94.02 | 0.17 | 6.02 |
| | 0.16 | 64.23 | 94.09 | 0.33 | 4.65 |
| | 0.24 | 67.19 | 94.12 | 0.36 | 4.02 |
| | 0.32 | 68.76 | 94.31 | 0.35 | 3.78 |
| Comparative 1 | 0.04 | 50.01 | 93.85 | −0.11 | 7.61 |
| | 0.08 | 56.60 | 94.01 | 0.16 | 6.27 |
| | 0.16 | 62.58 | 94.18 | 0.26 | 5.06 |
| | 0.24 | 65.75 | 94.24 | 0.30 | 4.40 |
| | 0.32 | 67.23 | 94.32 | 0.29 | 4.12 |

Thus, the FWAs used according to the invention exhibit same or even better whitening performance than a commonly used disulfo-type FWA while simultaneously having higher solubility in water, thus allowing the preparation of stable, concentrated aqueous preparations for whitening paper or board.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An aqueous fluorescent whitening agent preparations for optically whitening paper or board, comprising:

(a) 5 to 80% by weight of at least one fluorescent whitening agent (FWA) selected from the bis(triazinylamino)stilbene derivatives of the formula (I)

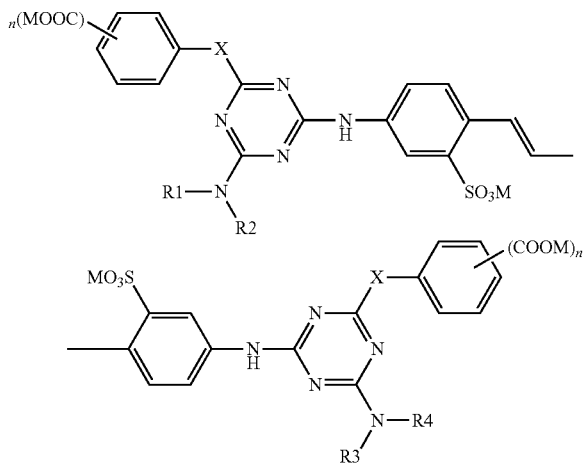

wherein

X represents NH;

n is 1 or 2;

$R_1$, $R_2$, $R_3$ and $R_4$ represent, independently of each other, hydrogen, cyano, $C_1$-$C_4$ alkyl, $C_2$-$C_4$ hydroxyalkyl, or $C_1$-$C_4$ alkoxyalkyl, wherein alkyl is linear or branched; or $R_2$ and $R_1$ or $R_3$ and $R_4$ independently of each other together with N atom form morpholine, piperidine or pyrrolidine ring; or —$(CH_2)_l$—$SO_3M$, where l is 1, 2 or 3; or —$(CH_2)_i$—COOR, —$(CH_2)_i$—CONHR, —$(CH_2)_i$—COR, where i is an integer from 1 to 4, R is $C_1$-$C_3$ alkyl or has the same meaning as M;

M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl; and (b) 95 to 20% by weight of water.

2. The aqueous fluorescent whitening agent preparations according to claim 1, wherein the preparation contains 10 to 65% by weight of component (a).

3. The aqueous fluorescent whitening agent preparations according to any of claim 1, wherein n is 1.

4. The aqueous fluorescent whitening agent preparations according to claim 1, wherein $R_1$, $R_2$, $R_3$ and $R_4$ represent, independently of each other, $C_2$-$C_4$ hydroxyalkyl, or $C_1$-$C_4$ alkoxyalkyl.

5. The aqueous fluorescent whitening agent preparations of claim 1, wherein the aqueous fluorescent whitening agent preparation contains less than 10% by weight of components other than components (a) and (b).

6. The aqueous fluorescent whitening agent preparations according to claim 1, wherein the fluorescent whitening agent has the following formula (Ia), wherein the carboxylic acid residues are, independently of each another, in ortho- or para-position

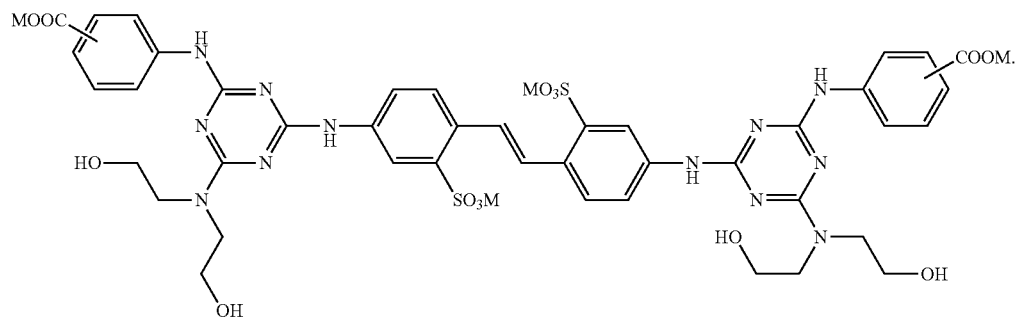

7. The aqueous fluorescent whitening agent preparations according to claim 1, wherein the fluorescent whitening agent has the following formula (Ib), wherein the carboxylic acid residues are, independently of each another, in ortho- or para-position.

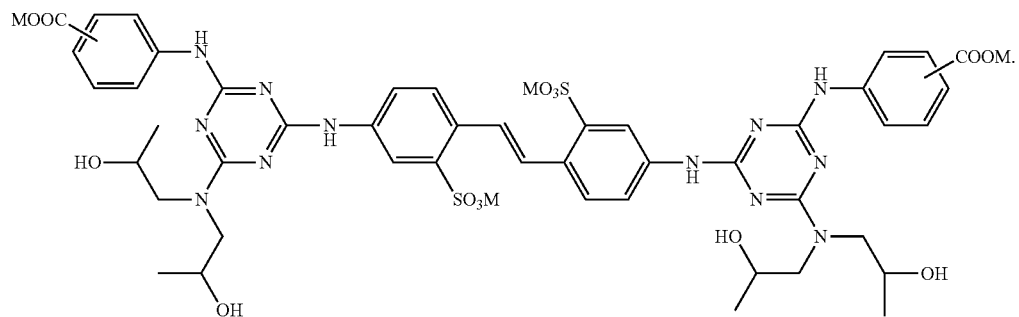

8. The aqueous fluorescent whitening agent preparations according to claim 1, wherein the aqueous fluorescent whitening agent preparation consists of the fluorescent whitening agent of formula (I).

9. The aqueous fluorescent whitening agent preparations according to claim 1, wherein the aqueous fluorescent whitening agent preparation contains two or three fluorescent whitening agents of formula (I).

* * * * *